United States Patent [19]

Heckele et al.

[11] Patent Number: 5,558,620
[45] Date of Patent: Sep. 24, 1996

[54] MEDICAL INSTRUMENT EMPLOYING CURVED SPREADING MEMBERS TO MANIPULATE ORGANS WITHIN THE BODY

[75] Inventors: Helmut Heckele, Knittlingen; Andreas Dingler, Birkenfeld; Ernst Falk, Sternenfels-Diefenbach, all of Germany

[73] Assignee: Richard Wolf GmbH, Knittlingen, Germany

[21] Appl. No.: 189,967

[22] Filed: Feb. 1, 1994

[30] Foreign Application Priority Data

Feb. 5, 1993 [DE] Germany .......................... 43 03 274.5

[51] Int. Cl.⁶ .................................................. A61B 17/02
[52] U.S. Cl. .......................... 600/208; 600/204; 600/205; 600/213; 606/198
[58] Field of Search ................................ 128/20, 17, 18; 604/104, 105, 106, 107, 108, 109; 606/191, 198

[56] References Cited

U.S. PATENT DOCUMENTS

| | | | |
|---|---|---|---|
| 1,031,314 | 7/1912 | Aber | 604/106 |
| 1,304,054 | 5/1919 | Imaizumi | 604/108 |
| 1,798,124 | 3/1931 | Hunn | 128/20 |
| 3,394,705 | 7/1968 | Abramson | 604/104 X |
| 4,909,789 | 3/1990 | Taguchi et al. | 606/198 X |
| 5,147,357 | 9/1992 | Rose et al. | |
| 5,195,505 | 3/1993 | Josefsen | 128/20 |
| 5,195,506 | 3/1993 | Hulfish | 128/20 |
| 5,235,966 | 8/1993 | Jamner | 128/20 |
| 5,293,863 | 3/1994 | Zhu et al. | 128/20 |
| 5,351,679 | 10/1994 | Mayzels et al. | 128/20 |
| 5,353,784 | 10/1994 | Nady-Mohamed | 128/20 |

FOREIGN PATENT DOCUMENTS

| | | | |
|---|---|---|---|
| 1723212 | 3/1956 | Germany | A81B 17/28 |
| 7808070U1 | 8/1978 | Germany | A61B 17/28 |
| 3709706A1 | 10/1987 | Germany | A61B 1/00 |
| 8709151U1 | 12/1987 | Germany | A61B 1/00 |
| 8801578U1 | 4/1988 | Germany | A61B 17/28 |
| 4021153A1 | 1/1992 | Germany | A61B 1/00 |
| 4125806A1 | 2/1993 | Germany | A61B 1/00 |
| 4216971 | 11/1993 | Germany . | |

Primary Examiner—Richard J. Apley
Assistant Examiner—Kelly McGlashen
Attorney, Agent, or Firm—Cohen, Pontani, Lieberman, Pavane

[57] ABSTRACT

An instrument for manipulating organs in endoscopic procedures in the interior of the body includes two spreading members at the distal end of the instrument. The spreading members can be swiveled outwardly and actuated by means of a handle at the proximal end of the instrument. A control member displaceably guided in the instrument shaft connects the handle and spreading members. The distal end of the instrument is bent in such a way that the spreading members spread out in a curved plane so that organs can be reliably guided with the manipulator.

15 Claims, 4 Drawing Sheets

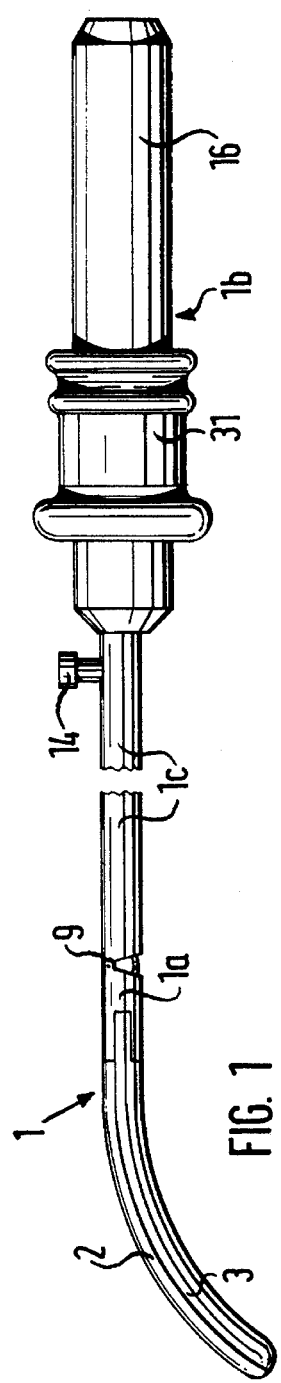
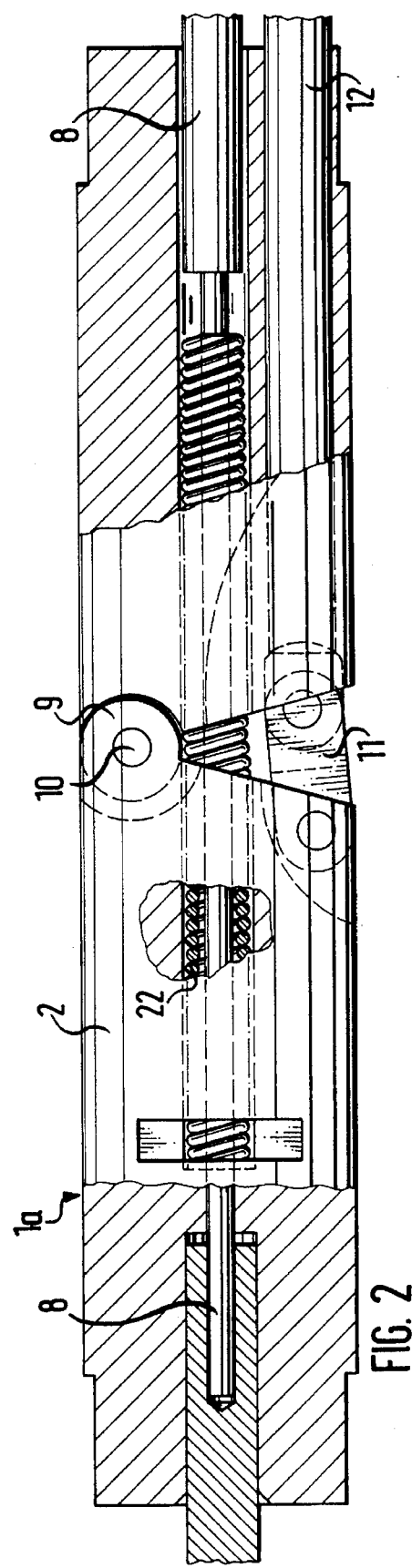

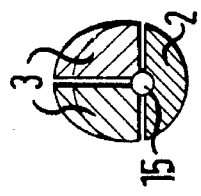
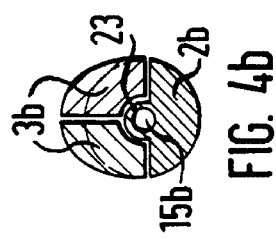
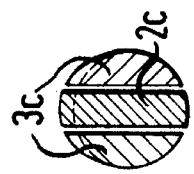
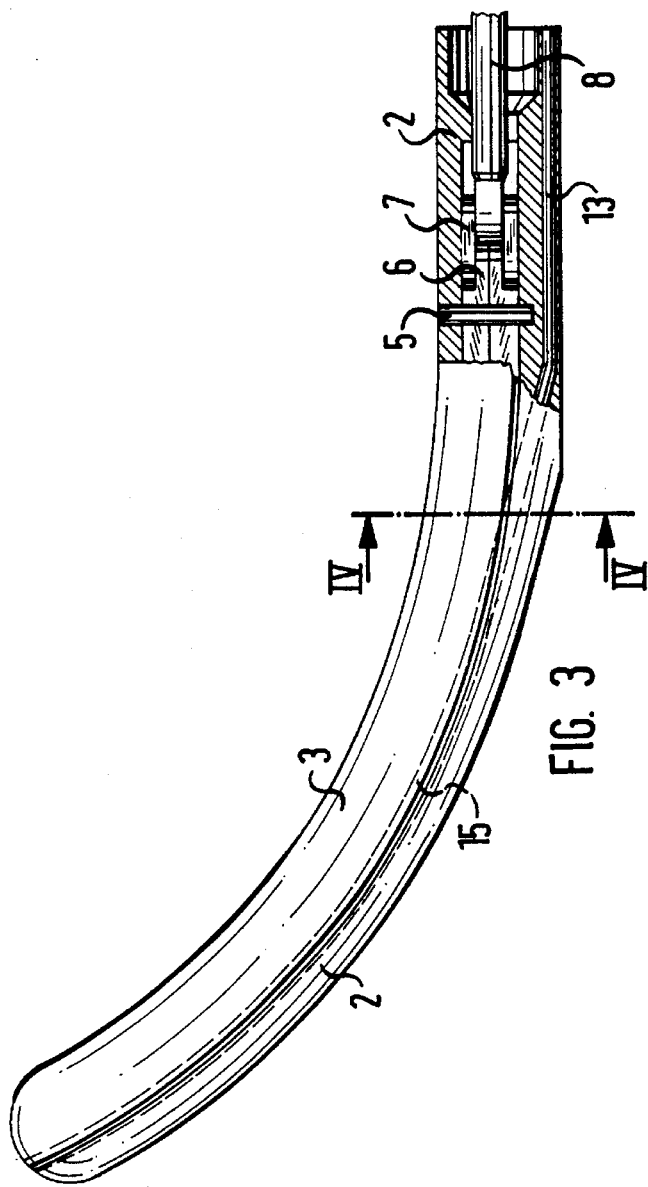
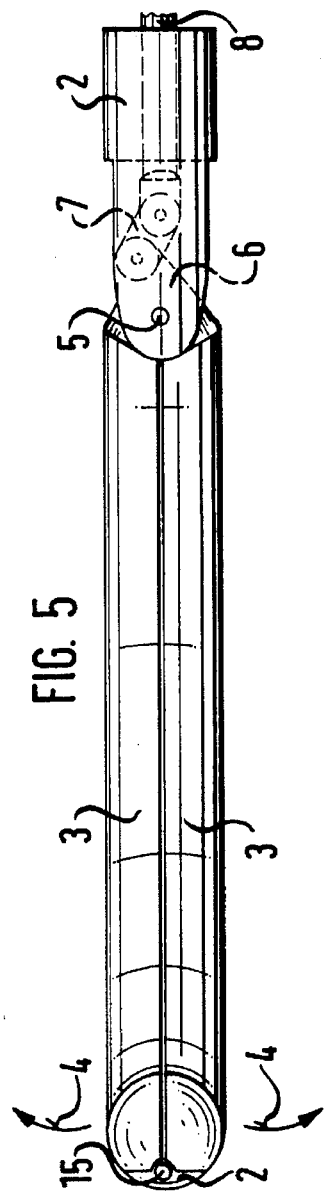

MEDICAL INSTRUMENT EMPLOYING CURVED SPREADING MEMBERS TO MANIPULATE ORGANS WITHIN THE BODY

BACKGROUND OF THE INVENTION

1. Field of the Invention

This invention relates generally to medical instruments, and more particularly, to an instrument for endoscopically manipulating organs in the interior of the body.

2. Description of the Prior Art

Instruments utilizing one or more spreading member(s) at the distal end thereof are used in particular in endoscopic procedures, e.g. in the abdominal cavity, to manipulate organs or other internal parts of the body, generally in order to bring the latter into a position and to maintain them in such a position that they do not cover or conceal the area to be examined or treated. Such instruments are subject to special requirements, since they should be as slender and smooth as possible on the one hand for the purpose of insertion into the body cavity and, on the other hand, should provide the best possible hold inside the body cavity. For this purpose, the instruments must be able to spread out over the largest possible surface area and also to transmit sufficient forces in this position, for example, to hold back a larger organ reliably. Further, the instruments must be constructed so as to exclude the risk of injury to a great extent, also in the spread out state.

An instrument of the generic type is known from DE 40 21 153 A1. This organ manipulator has proven successful in practical use. In particular, it satisfies the above-mentioned requirements to a great extent. This manipulator, which can be spread out in various positions, is generally used as a spatula, i.e. forces can be applied substantially only transversely to the surface spread out by the spreading members and, to a very limited extent, compressive forces may be applied in the direction from the proximal end to the distal end of the instrument. Essentially, the spreading members of this manipulator lie substantially in a common plane while they are in the "spread out" state. Disadvantageously, however, the organ to be manipulated typically has a spatially curved surface. Accordingly, high compressive loading may occur at points on the organ when the flat spreading members act on a sharply curved region of the organ. Additionally, it may not be possible to prevent the organ from slipping off the manipulator. Such slippage is highly undesirable and dangerous particularly when therapeutic procedures are in progress. Moreover, while it may be desirable in some applications to push the organ in one direction or the other, the conditions under which this is possible with the manipulator described above are very limited due to the risk of slippage.

An optical tissue hook is disclosed in DE 41 25 806 A1. This device has a shaft with a plurality of spreading elements which elements are arranged so as to be displaceable axially in the shaft. The spreading elements are pretensioned by means of a spring and have a double bend at the distal end. A hollow organ to be treated can be fixed and visually monitored by means of these spreading elements. This instrument is intended and suited exclusively for fixing a hollow organ at the abdominal wall, specifically by means of a clamping action between parts of the instrument. This instrument is not capable of the lateral displacement of organs mentioned above, e.g. for holding an organ away from a determined region of the body cavity.

Yet another endoscopic organ manipulator is disclosed in DE 37 09 706 A1. This manipulator has three resiliently elastic wires with spherical elements at their distal ends. These wires are pretensioned transversely to the longitudinal direction of the instrument in such a way that they spring out laterally when moved out of a sleeve tube so as to spread out in a spatial formation. This manipulator has the considerable disadvantage that it can exert only comparatively limited forces, since the wires deflect when loaded due to their springing action. The instrument is therefore unsuited for the area of use mentioned initially above.

It is therefore an object of the present invention to provide an instrument which avoids the aforementioned disadvantages associated with the prior art.

It is a further object of the present invention to provide an instrument which retains the characteristics and possibilities of use mentioned above and which also enables reliable lateral guidance of an organ, i.e. transversely to the axis of the instrument, without the risk of slippage.

It is yet another object of the present invention to provide an instrument which can also exert pulling forces on the organ, at least proportionally.

SUMMARY OF THE INVENTION

The aforementioned objects, as well as other benefits and advantages which will become apparent to those skilled in the art, are achieved by an instrument whose distal end includes a spreading member bent in such a way that a curved plane is spread out between the spreading member and a main body portion of the instrument in a spread out state or, if this end of the instrument should be made up exclusively of spreading members, between the spreading members.

In accordance with the invention, the distal end of the instrument and the spreading member arranged at the latter are fashioned in such a way that a reliable manipulation and guidance of the held organ in the interior of the body is ensured without the cross-sectional dimensions of the instrument being increased when the spreading members are swiveled in. This special shaping, as a result of which the end of the instrument suggests the shape of a flat hook or even a spoon in the spread out state, makes it possible not only to apply transverse forces to the organ, but also to hold the organ in such a way that the organ can be manipulated not only laterally, but also in diagonal directions.

In accordance with the present invention, one or more spreading members can be spread out from the rest of the main body of the instrument. Alternatively, two or more spreading members can form the distal end, of the instrument itself. In an illustrative embodiment, two spreading members are provided which are articulated in the vicinity of their proximal ends at the main body of the instrument or at the shaft of the instrument. The free distal ends of the spreading members can spread apart preferably toward opposite sides. Such an arrangement provides good handling due to the uniform distribution of forces on both sides. Moreover, it makes it possible to cover a comparatively large surface area relative to the axis of the instrument. In this case, the spreading members may be advantageously articulated at a common axis. However, if the plane spread out by the spreading members is curved not only in the direction of the axis of the instrument, but also transversely thereto, i.e. in the manner of a spoon, two axles are to be arranged at an angle relative to one another, e.g. at an acute angle of 10°.

In a construction in which the distal end of the instrument is formed exclusively by spreading members, as well as in a construction in which a main body of the instrument extends to this region, the spreading members and main body of the instrument are advantageously adapted to one another with respect to their cross-sectional shape in such a way that a round cross-sectional outer contour is formed in the swiveled in position so as to enable the easiest possible insertion into the body cavity.

For practical handling, the shaft of the instrument is advantageously constructed so as to be articulated prior to the spreading members, as viewed from the proximal to the distal end, so as to enable a retrograde angling of the distal end of the instrument together with the spreading members located on the latter. In this way a swiveling movement of the instrument can be carried out from the proximal end, i.e. the handle area, without having to change the position of the instrument. The joint axle should preferably be arranged transversely to the swivel axis of the spreading members. When the spreading members are swivelable around different axes, the joint axle should preferably be arranged transversely to the center swivel axis of all spreading members. Two joints may also be provided with swivel axles which are offset by 90° or a ball joint can be provided.

A suitable handle, which may be combined with the handle serving to control the spreading position so as to improve handling, is provided at the proximal end of the instrument to control the swiveling position of the joint. This swiveling position can be sensitively adjusted by means of a suitable handle. Due to the self-locking which results from an appropriate selection of thread pitch, a locking in the swiveling position is achieved at the same time so that the instrument remains fixed in this angular position without further steps.

The instrument according to the invention is advantageously provided with at least one duct having at the proximal end of the instrument a connection for receiving a probe or optical system or for rinsing or applying suction to bodily secretions or the like. In this way, it is possible not only to manipulate an organ with this instrument, but also, as the case may be, to rinse off areas in the body cavity or the endoscope and to apply suction or to undertake other therapeutic or diagnostic steps without using the endoscopic instrument. In terms of construction, this is accomplished by arranging a tube inside the actual instrument shaft, i.e. in the region between the proximal connection and the spreading members. Insofar as there remains a main body of the instrument in the region of the spreading members, this tube can be guided up to the distal end of the instrument. However, in a preferred construction, the tube passes into a duct in the region of the spreading members, this duct being defined by the inner sides of the main body of the instrument and/or spreading members. A variable cross section can be formed in this way. When the instrument is closed, i.e. when the spreading members are in the folded in position, the duct opens out at the distal end.

As was already mentioned, the outer contour of the instrument should be round, particularly in the region of the distal end. On the other hand, the sides of the spreading members which face one another are advisably constructed as plane sides so that they contact one another as if to form one piece in the folded in state. Such a construction provides the instrument with very great stability in the folded in state, particularly when the main body has a reinforcing or stiffening web extending between the spreading members. Naturally, the upper and lower plane surfaces are curved in the direction of the longitudinal axis of the instrument.

As mentioned above, the swivel axes of the spreading members can be arranged at an angle relative to one another if a plane curving in two directions is to be spread out. However, this is unnecessary as a rule, and a simplified configuration in which two or more spreading members are arranged at parallel swivel axles located in the main body of the instrument is preferred. The spreading members are lengthened beyond the axis in the proximal direction to form lever arms and their ends are connected in this location in an articulated manner with a control rod which is guided through the shaft of the instrument, this control rod being connected in a suitable manner with a handle at its proximal end. This control rod is advisably connected with a handle which can be displaced in a locking manner at the grip handle of the instrument so as to ensure a simple and reliable handling of the spreading function and to provide a locking function as well.

The elongated distal portion of the instrument is advantageously detachably connected with the proximal portion of the instrument having the handle via a coupling. Accordingly, it is possible to exchange the distal part of the instrument as required, e.g. for an instrument part with spreading members extending in a straight line. This has economical advantages in particular, since the grip part which contains all of the control functions of the instrument and is costly with respect to construction and manufacturing technique can be used for a number of different distal instrument parts.

The various features of novelty which characterize the invention are pointed out with particularity in the claims annexed to and forming a part of the disclosure. For a better understanding of the invention, its operating advantages, and specific object attained by its use, reference should be had to the drawing and descriptive matter in which there are illustrated and described preferred embodimemts of the invention.

BRIEF DESCRIPTION OF THE DRAWINGS

An understanding of the instrument of present invention will be facilitated by reference to the detailed description which follows along with the accompanying drawings in which:

FIG. 1 shows a simplified side view of an instrument according to the present invention;

FIG. 2 is an enlarged view in partial section of a portion of the distal end of the instrument as seen from the side;

FIG. 3 shows an enlarged side view of the distal part of the instrument, partly in section;

FIG. 4*a* shows a section along section line IV—IV in FIG. 3;

FIG. 4*b* shows a section corresponding to FIG. 4*a* in accordance with another embodiment of an instrument constructed in accordance with the present invention;

FIG. 4*c* shows a section corresponding to FIG. 4*a* in accordance with yet another embodiment of an instrument constructed in accordance with the present invention;

FIG. 5 depicts a top view of the distal end of the instrument according to FIG. 3;

DETAILED DESCRIPTION OF THE INVENTION

Figure 6:
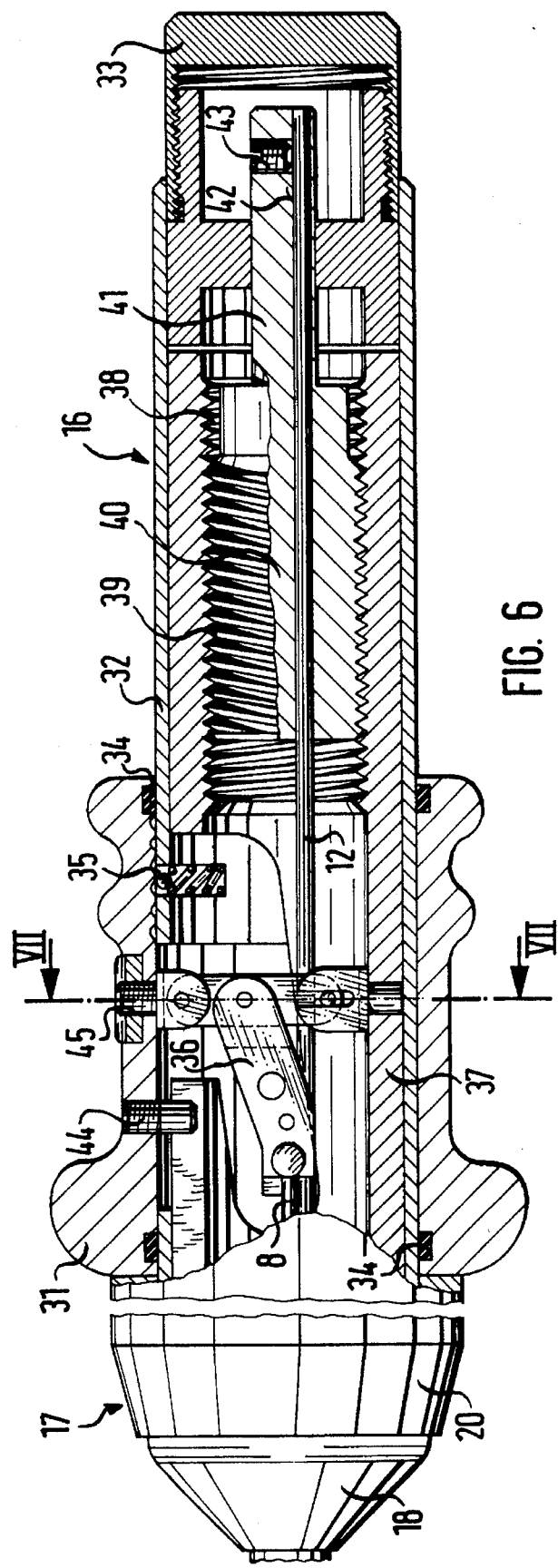
FIG. 6 illustrates a longitudinal section through the proximal part of the instrument.

With initial reference to FIG. 1, there is shown an illustrative embodiment of an instrument 1 constructed in accordance with the present invention. As seen in FIG. 1, instrument 1 comprises a distal instrument assembly 1a and a proximal instrument assembly 1b. The distal and proximal instrument assemblies are interconnected by instrument shaft 1c.

The distal instrument assembly 1a includes a main body portion 2 which is a prolongation of the tubular shaft 1c toward the distal end and has an approximately semicircular cross section of solid material (FIG. 4a). While the underside of the main body 2 of the instrument is rounded, its upper side is constructed as a planar surface, although it is curved in the axial direction of the instrument shaft (see FIGS. 3 and 5).

When the instrument constructed in accordance with the embodiment of FIGS. 14a and 5–7 is in the closed position, the corresponding undersides of two spreading members 3 are planar and curved in the axial direction of the instrument shaft so that they face the planar upper surface of main body 2. Spreading members 3 are likewise made of solid material. As best seen in FIG. 5, spreading members 3 also include opposed planar surfaces which are parallel to one another when the instrument is in the closed position. Preferably, the opposed planar surfaces of spreader members 3 contact one another in a flush manner so as to form with main body 2 an approximately round cross-sectional contour, as shown in FIG. 4a.

Spreading members 3 and main body 2 are bent or curved as viewed from the side (see FIG. 3). Returning to FIG. 5, it will be observed that a parallel joint axle 5 is fastened inside main body 2 and connects main body 2 with the spreading members 3. As will be readily appreciated by those skilled in the art, joint axle 5 defines a common swivelling axis. Accordingly, spreading members 3 can be swiveled out laterally in opposite directions as indicated by the arrows 4 so that the outer surfaces of the main body 2 and the spreading members 3 define a curved plane. Specifically, spreading members 3 are extended beyond the joint axle 5 in the direction of the proximal end 1b so as to form lever arms 6 by which the spreading members are articulated at the distal end of a first control rod 8 via intermediate levers 7. When the control rod 8 is moved in the distal direction, the spreading members 3 swivel out in the direction of the arrow 4.

A joint 9 around which the entire distal instrument assembly 1a can be swiveled is provided immediately before the distal articulation point of the first control rod 8 as viewed in the direction from the proximal end to the distal end of the instrument. The construction of this joint 9 and of the first control rod 8 in this region is best shown in FIG. 2. As seen in FIG. 2, joint 9 is arranged eccentrically relative to the shaft 1c. Moreover, joint axle 10 of joint 9 is arranged transversely to the joint axles 5 so that the entire distal assembly 1a of instrument 1 can be deflected around this joint axle 10 in a retrograde manner and, in this embodiment, only in one direction.

The first control rod 8 in the region of this joint may be advantageously constructed in the manner of a Bowden cable. The control rod 8 is resiliently flexible in this region and is surrounded by a helically wound supporting wire 22. The joint 9 is arranged in the vicinity of the outer side of the shaft 1c. The shaft 1c is recessed in a roughly V-shaped manner toward the opposite side proceeding from the joint 9, so as to provide the necessary clearance for bending. The distal assembly 1a is connected with a second control rod 12 in an articulated manner via an intermediate lever 11 in such a way that the distal assembly 1a is bent around the joint axle 10 when the control rod 12 is moved in the direction of the proximal end and is straightened again when the control rod 12 moves in the opposite direction.

With particular reference to FIG. 3, in addition to the two control rods 8 and 12, a tube 13 which is part of a suction/rinsing duct is also guided through the shaft 1c. This tube 13 ends on the proximal side in a line connection 14 (FIG. 1) which is guided out of shaft 1c laterally. At the distal side, this tube 13 opens into a duct 15 in the region of the spreading member 3, this duct 15 being formed in the closed position of the instrument by the insides of the spreading members 3 and those of main body 2 (FIG. 4a). Duct 15 opens out at the distal end of the instrument as shown in FIG. 5. When the spreading members are in the spread out position, this duct 15 does not exist. In this case, the suction/rinsing duct opens out at the distal end of the tube 13.

Two alternative embodiments of distal assembly 1a are explained with reference to FIGS. 4b and 4c. In the configuration depicted in FIG. 4b, the duct 15b is not defined by the inner sides of the spreading members 3b, but rather is guided inside the main body 2b as far as the distal tip of the instrument, so that the distal end of this duct 15b is independent from the position of the spreading members 3b. The main body 2b is constructed approximately in the shape of a T in this embodiment so as to form a stiffening web 23 which receives duct 15b and is contacted in a flush manner by the spreading members 3b (in the closed position of the instrument). This stiffening web 23 can have exactly the same thickness as the spreading members as seen in cross section, so that the web 23 (as shown in FIG. 4b) can define the instrument toward the top as well. Such a stiffening web provides for additional stability.

In the configuration depicted in FIG. 4c, the main body 2c of instrument 1 is constructed in the region of the spreading members as a narrow strip which lies between the inner sides of the spreading members and, according to the view in FIG. 4c, defines the cross section of the instrument in this region only at the top and the bottom.

Figure 8:
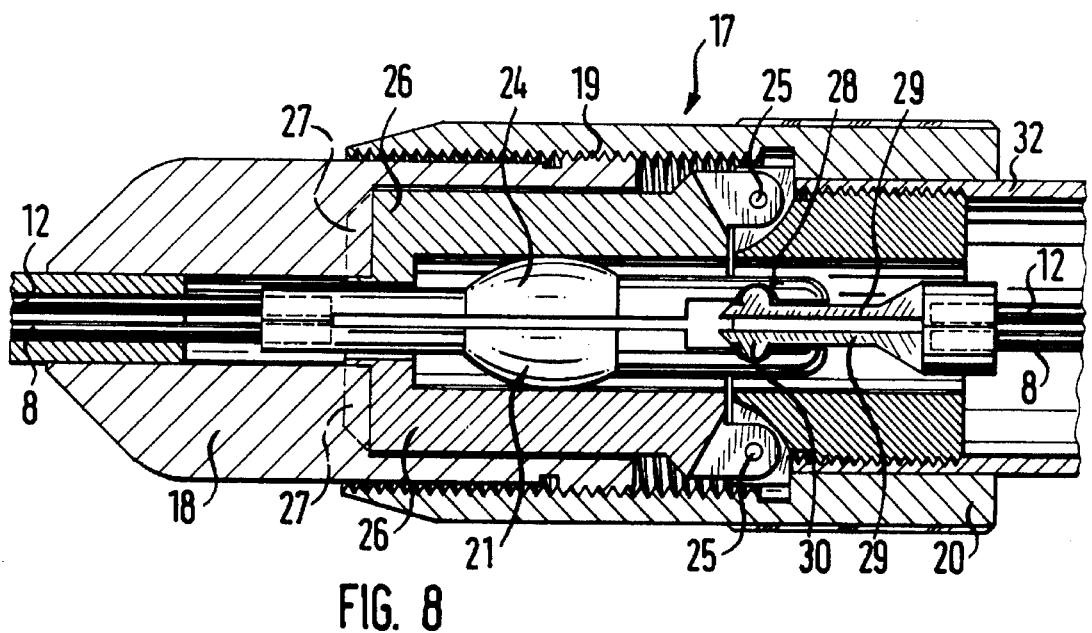
FIG. 8 shows a longitudinal section through the coupling between the distal and proximal parts of the instrument.

While the line connection 14 is guided out of the shaft 1c laterally prior to the grip element 16 arranged at the proximal end of the instrument, the control rods 8 and 12 are guided in as far as the grip element. As is shown in FIG. 8, a coupling 17 is provided in the distal region of the grip element 16. The instrument shaft 1c with the distal assembly 1a attached thereto is detachably connected with the proximal assembly 1b by means of coupling 17. At the proximal side, instrument shaft 1c passes into a cup-shaped element 18 which has an external thread 19 at its outer circumference in the proximal end region. External thread 19 is fastened to the grip element 16 by means of a knurled union nut 20 which is secured at the grip element 16.

Instrument shaft 1c is fixed in the cup-shaped element 18. Each control rod 8 and 12 has a coupling element 21, shown in FIG. 8, located inside this structural component. Every coupling element 21 has an enlarged diameter portion 24. Portions 24 are guided with slight play inside two connecting link halves which are supported at the grip element 16 so as to be swivelable around joint axles 25. These connecting link halves 26 in turn are secured in a positive-locking manner by the cup-shaped element in the assembled position according to FIG. 8 to prevent them from swiveling out radially. In order to ensure that the allocation between the control elements at the handle element 16 and the position of the distal assembly 1a remains identical after the connection of the coupling elements, two recesses 27 in which the distal ends of the connecting link halves 26 engage are provided inside the cup shaped element 18. When these ends lie in the recesses 27, the defined instrument position is achieved and the distal assembly is securely connected with the grip element.

A receptacle 28 in the approximate shape of a longitudinally divided sleeve with a half-annulus located therein is provided at the proximal end of every coupling element 21. A rod-shaped coupling element 29 engages in a positive-locking manner in the axial direction in each half of this receptacle 28. This coupling element 29 has at its distal end a half-torus 30 which lies in the aforementioned half-annulus in a positive-locking manner and accordingly ensures the axial transmission of force to the rod 8 and to the rod 12. As long as the coupling 17 is not yet locked, i.e. as long as the connecting link halves 26 can still swivel out, the receptacle 28 can be widened until the torus 30 lies in its intended position. The second control rod 12 is coupled in an analogous manner.

The distal end of the grip element 16 having the coupling 17 is shown in an abbreviated manner in FIG. 6, since this figure serves exclusively to explain the mechanical connection of the handle 31 with the rods 8 and 12. The grip element 16 has a cylindrical sleeve-shaped main body 32 which is terminated at the proximal side by a cover cap 33 and at the distal side by the elements 18 and 20 of the coupling 17. The annular handle 31 is supported on this main body 32 so as to be displaceable in the axial direction and rotatable. The axial displacement of the handle 31 serves to spread out and close the spreading members 3, i.e. to displace the control rod 8 axially. When the handle 31 is rotated relative to the main body 32, the swivel position of the distal assembly 1a is changed, i.e. the control rod 12 moves axially. Since the construction of the handle element 16 shown in FIG. 7 does not depend on whether the instrument is constructed with or without a coupling (as shown in FIG. 8), the control rods 8 and 12 are given the same reference numbers.

The annular handle 31 is sealed relative to the main body 32 at the ends via two seals 34. A catch device 35 is provided between the handle 31 and the main body 32, which is constructed as a housing, so that the handle 31 stays in the selected displaced position. The main body 16 has a recess in the region of the handle 31 which extends along 180°. Two pins 44, 45 which are securely connected with the handle 31 engage in this recess, one of them 45 being connected with the proximal end of the control rod 8 via a lever rod linkage. This proximal end is rotatably supported at the distal end of the angled lever 36. The lever rod linkage which is shown in detail in FIGS. 6 and 7 ensures that the axial displacement position is transmitted to the control rod 8 regardless of the rotational position of the handle 31.

A cylindrical sleeve 37 in which the aforementioned lever rod linkage is guided sits inside the main body 32. This sleeve 37 is rotatably supported inside the main body 16. The rotational position of the handle 31 is transmitted to this sleeve 37 by the pins 44, 45. In the proximal region beyond the handle 31, this sleeve 37, which is not displaceable axially inside the main body 16, has an internal thread 38 which communicates with the external thread 39 of a piston 40 which is supported so as to be displaceable axially inside the sleeve 37. This piston has an extension 41 in the proximal direction which ends in the portion covered by the cap 33 and is accordingly accessible when the cap 33 is removed. The piston 40 and the extension 41 are penetrated by a longitudinal bore hole 42 in which the control rod 12 is secured by means of a screw 43 (see FIG. 6). This screw serves to fix the basic position.

Figure 7:
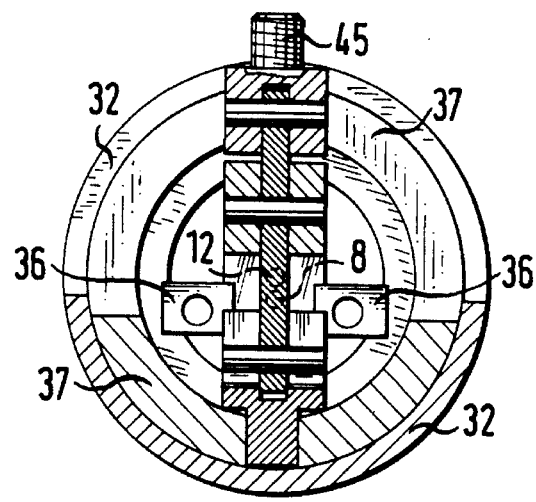
FIG. 7 shows a section along section line VII—VII in FIG. 6 (shown without the handle)

The handle 31 is rotatable relative to the housing 16 to the left or right by roughly 90° from the middle position shown in FIG. 7. This causes the sleeve 37 which is supported inside the main body 16 to be rotated so that the piston 40 which is supported so as to be fixed with respect to rotation relative thereto is displaced axially. In this way, the control rod 12 is also displaced axially and the swiveling position of the joint 9 is accordingly changed. Thus, the handle 31 enables a central operation of the instrument with the use of only one hand.

Although the present invention has been described in detail, it should be understood that various changes, substitutions, and alterations can be made herein without departing from the spirit and scope of the present invention. For example, the instrument can be optionally configured either with or without coupling. The stationary main body 2 of the instrument may also be dispensed with in its entirety in the region of the spreading members 3 if so desired. The number of spreading members can be adjusted as needed. If desired, the control rods 8 and 12 can also be adjusted by an electric motor. In this case, corresponding switches would be located at the grip element 16 instead of the handle 31. Accordingly, it is intended that the scope of the present invention be limited only by the appended claims.

The invention is not limited by the embodiments described above which are presented as examples only but can be modified in various ways within the scope of protection defined by the appended patent claims.

What is claimed is:

1. A medical instrument for manipulating organs within the body of a patient, comprising:

an instrument shaft having a longitudinal axis;

an main body portion disposed at the distal end and constituting a prolongation of said instrument shaft, and at least one spreading member mounted at the distal end of said instrument shaft by a pivot axle perpendicular to the longitudinal axis of the instrument shaft so that said spreading member is pivotable relative to the non-moving said main body portion about the pivot axle between non-spread out and spread out positions; and handle means for pivoting said spreading member about said pivot axle, said handle means including a handle disposed at the proximal end of said instrument shaft and at least one control member interconnecting said spreading member and said handle, said control member being displaceably guided within said instrument shaft such that said spreading member pivots about said pivot axle in response to movement of said handle means, wherein said main body portion and said at least one spreading member are curved so that outer surfaces thereof define a curved support plane when said spreading member is in the spread out position.

2. A medical instrument according to claim 1, wherein at least two spreading members are included, said spreading members being respectively pivotable relative to said main body portion to define a spread apart position in which a corresponding distal end of each spreading member is on an opposite side of said main body portion.

3. A medical instrument according to claim 1 or 2, wherein said main body portion and said at least one spreading member define a round cross-sectional outer contour when said at least one spreading member is in the non-spread out position.

4. A medical instrument according to claim 1, further comprising means for pivotably coupling the main body portion to the instrument shaft, said coupling means including a joint axle arranged transversely to said pivot axle, whereby said main body portion and said at least one spreading member may be swivelled relative to a longitudinal axis of the instrument shaft.

5. A medical instrument according to claim 4, further comprising second handle means for controlling swivelling of the main body portion about said joint axle.

6. A medical instrument according to claim 1, further including a duct extending longitudinally within the instrument between proximal and distal ends thereof.

7. A medical instrument according to claim 1, wherein two spreading members are included and wherein respective side surfaces of the spreading members abut one another and respective lower surfaces thereof are supported by a planar upper side surface of said main body portion when said spreading members are in the non-spread out position.

8. A medical instrument according to claim 7, axle interconnects the spreading members with the main body portion and wherein said control member comprises a control rod guided through the instrument shaft, a portion of each spreading member being adapted to project out over the pivot axle in a proximal direction so as to form a corresponding lever arm and said spreading members are articulated by said control rod. members are articulated by said control rod.

9. A medical instrument according to claim 8, further including a grip and wherein said control rod is connected to said handle, said handle being axially displaceable relative to said grip and being lockable with respect thereto.

10. A medical instrument according to claim 1, wherein a first and a second spreading member are mounted to the instrument shaft, said main body portion having a stiffening web which extends between said first and second spreading members and contacts inner side surfaces of the spreading members in said non-spread out position.

11. A medical instrument according to claim 1, further including a coupling for detachably coupling the instrument shaft to said handle.

12. A medical instrument according to claim 6, wherein said duct has a first portion and a second portion, the first portion of said duct comprises a tube extending from the proximal end of the instrument and terminating proximate said at least one spreading member, said main body portion defining the second portion of said duct in fluid communication with said tube.

13. A medical instrument according to claim 12, wherein the second portion of said duct extends to the distal end of the main body portion.

14. A medical instrument for manipulating organs within the body of a patient, comprising:

an instrument shaft having a longitudinal axis;

a main body portion disposed at the distal end of said instrument shaft, and a plurality of spreading members mounted at the distal end of said instrument shaft by a pivot axle perpendicular to the longitudinal axis of the instrument shaft so that said spreading members are pivotable relative to said main body portion about the pivot axle between no-spread out and spread out positions;

handle means for pivoting said spreading members about said pivot axle, said handle means including a handle disposed at the proximal end of said instrument shaft and at least one control member interconnecting said spreading members and said handle, said control member being displaceably guided within said instrument shaft such that said spreading members pivot about said pivot axle in response to movement of said handle means, wherein said main body portion and said spreading members are curved so that outer surfaces thereof define a curved plane when said spreading members are in the spread out position; and a duct extending longitudinally within the instrument between proximal and distal ends thereof, a first portion of said duct comprises a tube extending from the proximal end of the instrument and terminating proximate the plurality of spreading members, aligned interior surfaces of said spreading members and said main body portion in said non-spread out position defining a second portion of said duct in fluid communication with said tube.

15. A medical instrument according to claim 14, wherein the duct terminates at the distal end of said instrument.

* * * * *